United States Patent [19]

Steer

[11] Patent Number: 4,940,461
[45] Date of Patent: Jul. 10, 1990

[54] FILTER FOR ATTACHMENT TO AN OSTOMY BAG

[75] Inventor: Peter L. Steer, Surrey, England

[73] Assignee: E. R. Squibb & Sons, Inc., Princeton, N.J.

[21] Appl. No.: 267,466

[22] PCT Filed: Mar. 1, 1988

[86] PCT No.: PCT/GB88/00149
§ 371 Date: Oct. 24, 1988
§ 102(e) Date: Oct. 24, 1988

[87] PCT Pub. No.: WO88/06433
PCT Pub. Date: Sep. 7, 1988

[30] Foreign Application Priority Data

Mar. 2, 1987 [GB] United Kingdom ............... 8704826

[51] Int. Cl.⁵ .................................... A61F 5/44
[52] U.S. Cl. ........................ 604/333; 55/385.4
[58] Field of Search .............. 604/332, 333; 215/224; 55/385.4, DIG. 13

[56] References Cited

U.S. PATENT DOCUMENTS

| | | | |
|---|---|---|---|
| 3,850,326 | 11/1974 | Ryles | 215/224 |
| 4,411,659 | 10/1983 | Jensen et al. | 604/332 |
| 4,451,258 | 5/1984 | Jensen | 604/333 |
| 4,460,363 | 7/1984 | Steer et al. | 604/336 |
| 4,460,392 | 7/1984 | Poulsen et al. | 604/333 |
| 4,516,974 | 5/1985 | Davis | 604/333 |
| 4,668,258 | 5/1987 | Steer | 55/387 |
| 4,723,951 | 1/1988 | Steer | 604/333 |

FOREIGN PATENT DOCUMENTS

| | | |
|---|---|---|
| 1571657 | 7/1980 | United Kingdom . |
| 2116433 | 9/1983 | United Kingdom . |
| 2122090 | 1/1984 | United Kingdom . |
| 2177301 | 1/1987 | United Kingdom . |
| 2177924 | 2/1987 | United Kingdom . |
| 2177926 | 2/1987 | United Kingdom . |
| 2193097 | 2/1988 | United Kingdom . |
| 2193098 | 2/1988 | United Kingdom . |

Primary Examiner—Stephen C. Pellegrino
Assistant Examiner—Michael Rafa
Attorney, Agent, or Firm—Stephen B. Davis

[57] ABSTRACT

A three part filter is provided for attachment to an ostomy bag. One part includes a synthetic plastics base member having a central aperture and one flat surface whereby the filter can be attached to the bag wall. There are two walls upstanding from the other side of the base member to define a channel. The inner wall defines a shallow recess. The second part is a pad of filtering medium. The third part is a lid member of synthetic plastics material, with apertures through its top wall; the lid being a snug push fit within the channel. With this arrangement the lid member is readily removable to allow replacement of the filter pad.

3 Claims, 3 Drawing Sheets

FILTER FOR ATTACHMENT TO AN OSTOMY BAG

This invention relates to a filter for attachment to an ostomy bag.

There has been proposed, in our U.K. Patent Application Serial No. 2 177 926, a filter housing forming part of a bag side element of an ostomy coupling. Within this filter housing is received a disc of a filter medium. One example of a suitable filter element is that disclosed and claimed in out U.K. Patent Application Serial No. 2 171 052. While in many circumstances it is convenient to have a filter housing integral with a bag side coupling element, for certain kinds of ostomy and similar bags for receiving discharged waste material from the human body, it is desirable to have a filter which is particularly adapted to be attached to the wall of an ostomy bag. One method of attachment is the use of an adhesive patch filter and another arrangement is the employment of a fold-over filter, see our U.K. Patent 2 122 090. In contrast to these suggestions, the present invention aims to meet the need for a filter which can be permanently attached to the bag but which nevertheless permits exchanging the filter medium.

According to the present invention, there is provided a filter for attachment to an ostomy bag and which comprises three parts, the first part including a synthetic plastics base member having a central aperture therein and one substantially flat surface whereby the filter can be attached by plastics welding or adhesive to a wall of the ostomy bag, there being two walls upstanding from the other side of the base member to define a channel and the inner wall defining with the base member a shallow recess, the second part being a pad consisting essentially of a filtering medium and having a height substantially equal to that of the recess and lateral dimensions such that it fits snugly within the recess, and the third part being a lid member of synthetic plastics material having a substantially flat top through which are provided a peripheral array of apertures, there being a wall extending from the flat top and having such a height, shape and width that it is a snug push fit within the channel; whereby the lid member is readily removable to allow replacement of the said pad.

In a preferred embodiment of the invention the channel and the wall on the lid member are of substantially circular formation.

In an advantageous embodiment of the invention, the wall on the lid member and/or one or both of the walls on the base member has a projection or a series of projections. These projections are positioned and dimensioned such that a snap fit can be achieved between the base and the lid members, and such that these members can be separated manually quite readily by the wearer.

In a particularly preferred embodiment of the invention, the lid member has a circular array of apertures located adjacent to and interiorly of the wall thereon, said wall being substantially cylindrical in shape so as to define a shallow cylindrical recess for receiving the filter medium in the form of a disc.

The wall on the lid member may have a radially outwardly extending rim so as to enhance its snap fit co-operation with the aforesaid channel.

The invention will be better understood from a consideration of the following description of an illustrative embodiment thereof, given with reference to the accompanying drawings, in which.

Figure 1:
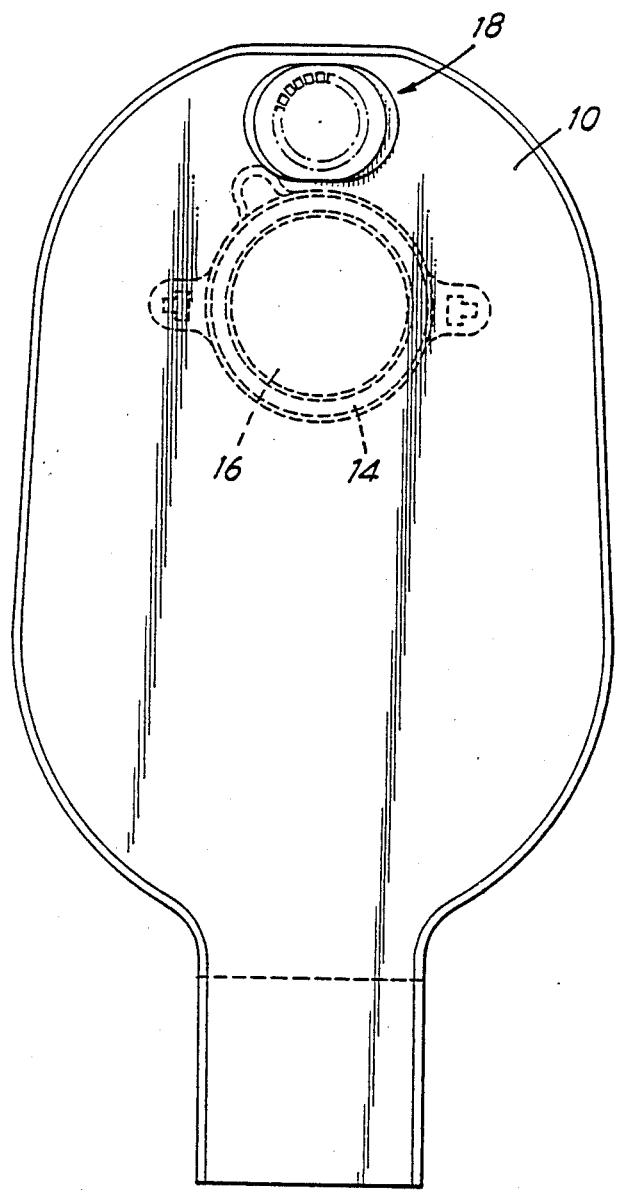
FIG. 1 is a front view of an ostomy bag including a filter in accordance with one example of the present invention.
Figure 2:
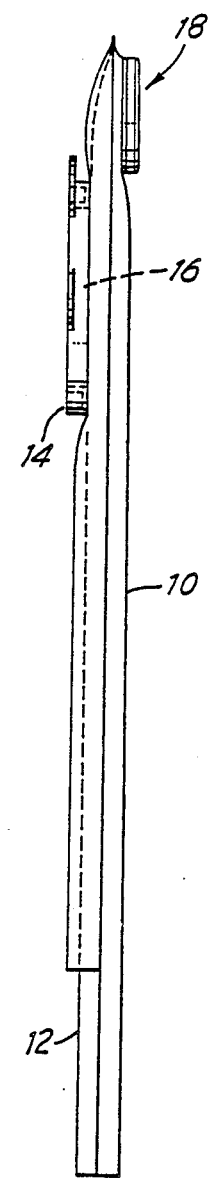
FIG. 2 is a diagrammatic side view of the ostomy bag shown in FIG. 1.
Figure 3:
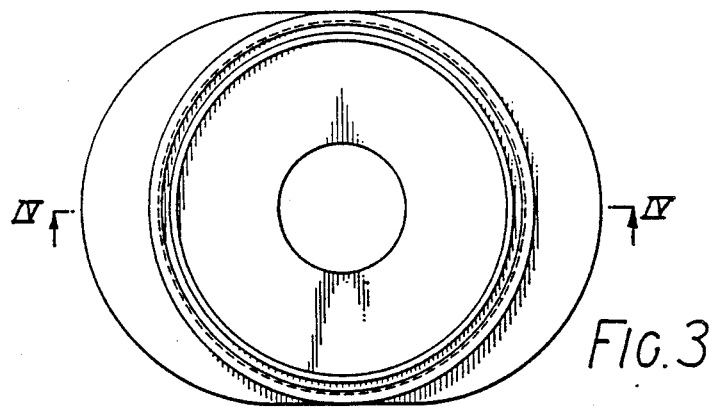
FIG. 3 is a front view of the base member of an example of filter in accordance with the present invention.

The illustrated ostomy bag has a front wall 10 and a rear wall 12. Front and rear are used in the context of a forward facing person wearing an ostomy bag on a forward part of his abdomen. The rear wall 12 of the ostomy bag carries a bag side ostomy coupling. This is intended to co-operate with a body side coupling in a manner now well known in the art, see for example Britsh Patent 1 571 657. The bag side coupling is shown at 14. It surrounds a stomal aperture 16 in the wall of the bag. The front wall 10 carries a filter 18 in accordance with the present invention. Details of the filter will be better understood from FIGS. 3–9.

The filter includes a first part or base member 20, a filter pad 30, and a lid member or third part 40.

The base member 20 is of synthetic plastics material and has a central aperture 21 therein and one substantially flat surface 22 whereby the filter can be attached by plastics welding or adhesive to the wall 10 of the ostomy bag.

Figure 4:
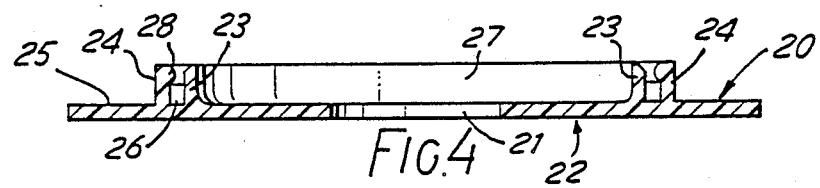
FIG. 4 is a cross-sectional view on a line 4—4 in FIG. 3 of the base member.

Two walls 23, 24 are upstanding from the other side 25 of the base member of define a channel 26 therebetween. The inner wall defines with the base member a shallow recess 27. In the illustrated embodiment of the invention, the walls 23 and 24 are generally circular and the recess is of a shallow cylindrical shape. However, the advantages of the invention do not necessarily require a circular configuration for the walls and a cylindrical recess, other shapes may be employed as will be understood by a man of average skill in the art. The outer wall 24 as seen in FIG. 4, has an internal peripheral rim or projection 28.

Figures 5, 6:
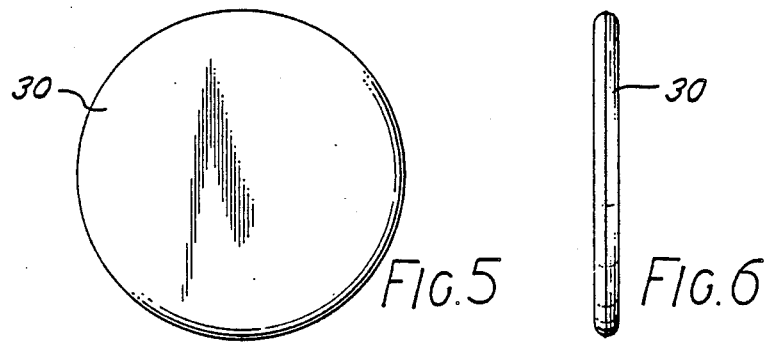
FIG. 5 and FIG. 6 are respectively a front view and a side view of a filter pad for use in a filter according to the present invention.
Figure 7:
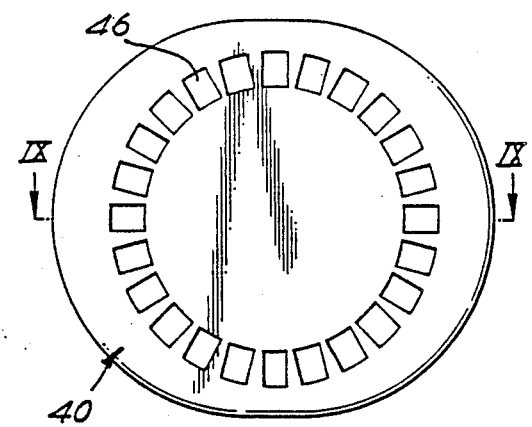
FIG. 7 is a front view of a lid member for use in a filter according to the present invention.
Figure 8:
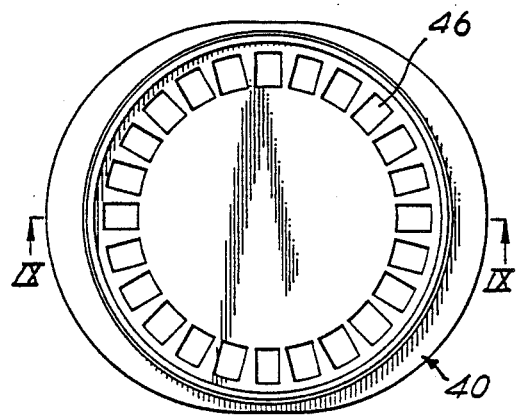
FIG. 8 is a rear view of the lid member shown in FIG. 7.
Figure 9:
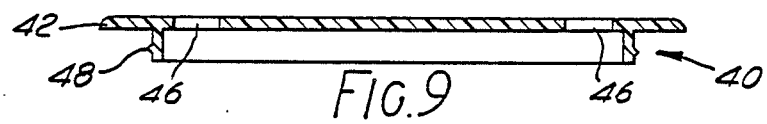
FIG. 9 is a cross-sectional view on the lines IX—IX of FIGS. 7 and 8.

The second part shown in FIGS. 5 and 6 is a filter pad of suitable material which permits a passage of gases. It may carry activated carbon as filter material. Any known suitable filter pad or disc may be employed but a particularly advantageous one is that diclosed and claimed in our British Patent Application Serial No. 2 171 052.

The third part of the illustrated filter according to the present invention is the lid member 40, and this has a generally flat lid portion 42 and a cylindrical wall 44 extending therefrom. It also has a series of apertures 46 arranged to provide a plurality of peripherally arranged exit paths for filtered gas to pass to the exterior. These apertures are shown at 46. As illustrated, the wall 44 has a peripheral external rim or projection 48 at its end further from the lid portion 42. The projection 48 is pushed past the projection 28 on the wall 24 when the wall 44 is inserted into the channel 26 as occurs when the lid is placed on the base member. The presence of the projections described gives a secure attachment of the lid to the base member but nevertheless this construction is an arrangement in which an easy manual separation of these two parts can be obtained, e.g. when it is desired to change the filter disc in the recess 27.

I claim:

1. A filter for attachment to an ostomy bag and which comprises three parts, the first part including a synthetic plastics base member having a central aperture therein and one substantially flat surface whereby the filter can be attached by plastics welding or adhesive to a wall of the ostomy bag, there being two walls upstanding from the other side of the base member to define a channel and the inner wall defining with the base member a shallow recess, the second part being a pad consisting essentially of a filtering medium and having a height substantially equal to that of the recess and lateral dimensions such that it fits snugly within the recess, and the third part being a lid member of synthetic plastics material having a substantially flat top through which are provided a peripheral array of apertures to provide fluid communication directly directly between ambient atmosphere and said recess, therebeing a wall extending from the flat top and having such a height, shape and width that it is a snug push fit within the channel; whereby the lid member is readily removable to allow replacement of the said pad, said wall on the lid member and one or both of the walls on the base member having a projection or a series of projections whereby a snap fit can be achieved between the base and lid members, said peripheral array of apertures being located adjacent to and interiorly of the wall of said lid.

2. A filter according to claim 1 in which the channel and the wall on the lid member are of substantially circular formation.

3. A filter according to claim 1 in which the wall on the lid member has a radially outwardly extending rim.

* * * * *